United States Patent
Warrior et al.

(10) Patent No.: US 6,942,860 B2
(45) Date of Patent: Sep. 13, 2005

(54) METHOD FOR PRODUCING A NEMATOCIDAL COMPOSITION BY HEAT TREATING A PH-ADJUSTED FERMENTATION BROTH

(75) Inventors: Prem Warrior, Green Oaks, IL (US); Daniel Feulner Heiman, Libertyville, IL (US); Linda Anne Rehberger, Glenview, IL (US); Ronald Eugene Johnson, Grayslake, IL (US); James Russell Hansen, Bensenville, IL (US); Kevin Allen McVicker, Palos Park, IL (US)

(73) Assignee: Valent BioSciences Corporation, Libertyville, IL (US)

( * ) Notice: Subject to any disclaimer, the term of this patent is extended or adjusted under 35 U.S.C. 154(b) by 353 days.

(21) Appl. No.: 10/357,809

(22) Filed: Feb. 4, 2003

(65) Prior Publication Data

US 2003/0215480 A1 Nov. 20, 2003

Related U.S. Application Data

(62) Division of application No. 09/829,603, filed on Apr. 10, 2001, now Pat. No. 6,540,998.
(60) Provisional application No. 60/196,257, filed on Apr. 11, 2000.

(51) Int. Cl.$^7$ ............................................. A61K 35/00
(52) U.S. Cl. ................... 424/115; 424/780; 424/195.16; 424/405
(58) Field of Search ................... 424/115, 780, 424/195.16, 405

(56) References Cited

U.S. PATENT DOCUMENTS

| | | | |
|---|---|---|---|
| 4,229,442 A | 10/1980 | Pinckard | |
| 4,883,759 A | 11/1989 | Hopkins | |
| 5,051,255 A | 9/1991 | Devidas et al. | |
| 5,057,141 A | 10/1991 | Rodriquez-Kabana et al. | |
| 5,182,207 A | 1/1993 | Ward et al. | |
| 5,360,607 A | 11/1994 | Eyal et al. | |
| 5,439,934 A | 8/1995 | Wood et al. | |

*Primary Examiner*—Jean C. Witz
(74) *Attorney, Agent, or Firm*—Wood, Phillips, Katz, Clark & Mortimer

(57) ABSTRACT

The present invention is directed to a method for producing a new nematocidal composition particularly useful against plant parasitic nematodes and also a process to prevent damage resulting from nematode infestation. The method for production of the composition involves heating a pH-adjusted fermentation broth of microorganisms to a temperature of at least about 100° C. for at least about 15 minutes. Preferably, the microorganism is *Gibberella fujikuroi*, *Streptomyces erythraeus*, *Bacillus sphaericus*, *Bacillus thuringiensis* or *Fusarium moniliforme*.

20 Claims, No Drawings

METHOD FOR PRODUCING A NEMATOCIDAL COMPOSITION BY HEAT TREATING A PH-ADJUSTED FERMENTATION BROTH

This application is a division of application Ser. No. 09/829,603 filed Apr. 10, 2001, now U.S. Pat. No. 6,540,998, which claims the benefit of Provisional application Ser. No. 60/196,257, filed Apr. 11, 2000.

FIELD OF THE INVENTION

The present invention is directed to a method for producing a new nematocidal composition particularly useful against plant parasitic nematodes and also a process to prevent damage resulting from nematode infestation. The method for production of the composition involves heating a pH-adjusted fermentation broth of microorganisms to a temperature of at least about 100° C. for at least about 15 minutes.

BACKGROUND OF THE INVENTION

Plant parasitic nematodes cause serious economic damage to many agricultural crops around the world. The nematodes in this group are microscopic worms and are, in general, obligate parasites of plants. They feed mostly on the roots of host plants; however, several genera are known to parasitize above-ground parts including stems, leaves and flowers as well. Almost all the plant species of economic importance are susceptible to infection by some species of nematodes (notable exceptions are in the marigolds and asparagus). For example, root knot nematodes (RKN), (*Meloidogyne* spp.) are capable of parasitizing more than 3,000 species of crop plants. These plants include agronomic crops, vegetables, fruits, flowering trees and shrubs. Nematodes reportedly cause crop loss equivalent to more than six billion dollars in the United States alone and more than one hundred billion dollars around the world.

The symptoms due to parasitic nematode injury vary widely depending on the plant host, the nematode species, age of the plant, geographical location and climatic and external environmental conditions. In general, an overall patchy appearance of plants in a field is considered indicative of nematode infestation. More specifically, nematode injury results in galling of the roots (abnormal swelling in the tissue due to rapid multiplication of cells in the cortical region) caused by species of root knot (*Meloidogyne* spp.) and cyst (*Heterodera* spp.) nematodes, lesions (localized, discolored areas) caused by lesion nematodes (*Pratylenchus* spp.), suppression of cell division resulting in stubby roots (*Trichodorus* spp.), growth abnormalities including crinkling or twisting of above-ground parts (*Aphelenchoides* spp.), and even cell necrosis (death) in some cases. Plant parasitic nematodes may be endoparasitic in nature, as in the case of the root-knot and lesion nematodes, or ectoparasitic as in the dagger nematode (*Xiphinema* spp.) and lance nematode (*Hoplolaimus* spp.). Nematodes can be vectors of plant viruses and are also known to induce disease complexes predisposing plants to infection by other plant pathogenic fungi and bacteria.

Chemical nematocides, either soil fumigants or non-fumigants, have been in use for many years and are among the few feasible options for countering nematodes. At present, the process involves repeated applications of synthetic chemicals to the ground prior to planting the crop. These chemicals are extremely toxic to organisms besides nematodes and many of them may pose serious threats to the environment. With the renewed emphasis on clean water and air by environmental groups and governmental agencies, and the detection of many of these active ingredients or the metabolites thereof in ground water and several non-target organisms, there has been serious concern as to the manufacture and/or use of these chemicals. One of the most effective, economical, and widely used nematocides, DBCP (1,2-dibromo-3-chloropropane), found in ground water has been judged to induce male sterility and possible carcinogenesis. Another widely used chemical, EDB (ethylene dibromide), has also been found in ground water. Yet another very common insecticide-nematocide, aldicarb (2-methyl-2-(methylthio)-propionaldehyde-O-(methylcarbamoyl) oxime), has been found to be acutely toxic. Aldicarb has been found in ground water in several regions of United States. Carbofuran (2,3-dihydro-2,2-dimethyl-7-benzofuranyl methylcarbamate) and 1, 3-D (1,3-dichlorpropane), two very commonly used nematocides, are under special review by EPA because of their avian toxicity and possible carcinogenic effects. More recently, the decision by EPA to limit and eventually discontinue the use of the soil fumigant, methyl bromide, for agricultural purposes presents a threat to the efficiency and quality of agricultural production in the United States.

Natural isolates such as N-acetyl-D-glucosamine, which may be derived from microorganisms which are the waste products of industrial fermentation processes, have been disclosed as nematocidal in U.S. Pat. No. 5,057,141.

Biopesticides have been developed as an alternative to chemical pesticides. They are obtained by fermentation and can be used either as crude biomass or purified. Typically, fermentations are carried out at temperatures in the range of 20–40° C. For example, submerged fermentation at 28–30° C. of *Paecilomyces fumosoroues* fungal isolate ATCC No. 20874 produces fungal biomass for control of nematode infestation as disclosed in U.S. Pat. No. 5,360,607; whole fermentation broth from fermentation at 28° C. of *Streptomyces thermoarchaensis* NCIB 12015 is disclosed as nematocidal in U.S. Pat. No. 5,182,207; fermentation broth obtained from fermentation of *Streptomyces cyaneogriseus* noncyanogenus NRRL 15773 at 28° C. is effective against nematodes as disclosed in U.S. Pat. No. 5,439,934; and fermentation broth obtained by fermentation of the fungus *Myrothecium verrucaria* at temperatures of from 25 to 30° C. is disclosed as nematocidal in U.S. Pat. No. 5,051,255.

Heating of an infested biomass, as disclosed in U.S. Pat. No. 4,229,442, at a temperature of at least 125° C. with water in an amount ranging from 1–5 times the dry weight of the biomass, may combat nematodes.

However, there is still a need for the development of new and effective nematocides. It is therefore an object of this invention to provide a method for the production of nematocidal compositions which are effective and inexpensive.

BRIEF SUMMARY OF THE INVENTION

The invention is directed to a method of producing a nematocide from fermentation broths of microorganisms by heating a fermentation broth to a temperature of at least about 100° C. after adjusting the pH to about pH 2 or below, or about pH 8 or above. The nematocide thus produced can be used to prevent plant damage and/or limit the growth of nematodes.

The present invention is directed to a method for improving biopesticidal activity of materials produced by fermentation comprising the steps of:

fermenting a bacterium or fungus to obtain a fermentation broth;

adjusting the pH of said fermentation broth to a pH of below about 2.5 with a biologically acceptable acid, or to a pH of above about 8 with a biologically acceptable alkali or base; and heat treating said fermentation broth to a temperature of at least about 100° C. for at least about 15 minutes, then cooling to ambient temperature to obtain a pH-adjusted, heat treated composition having improved biopesticidal activity;

with the proviso that said fungus is not *Myrothecium verrucaria* when the pH of said fermentation broth is adjusted to a pH of below about 2.5.

The invention is also directed to a composition comprising a heat-treated, pH adjusted fermentation broth of a fungus or bacterium selected from the group consisting of *Gibberella fujikuroi, Streptomyces erythraeus, Bacillus sphaericus, Bacillus thuringiensis* and *Fusarium moniliforme;* wherein said broth is pH adjusted either to a pH of below about 2.5 with a biologically acceptable acid, or to a pH of above about 8 with a biologically acceptable alkali or base;

and wherein said broth is heated to a temperature of at least about 100° C. for at least about 15 minutes, then cooled to ambient temperature.

The invention is also directed to a method for control of nematodes on plants which comprises the step of administering to the locus, soil or seed of plants in need of such treatment, a nematocidally effective amount of a composition formed by heating a pH adjusted fermentation broth from a fungus or bacterium;

wherein said broth is adjusted to a pH of below about 2.5 with a biologically acceptable acid, or to a pH of above about 8 with a biologically acceptable alkali or base;

and wherein said broth is heated to at least 100° C. for at least 15 minutes;

with the proviso that said fungus is not *Myrothecium verrucaria* when the pH of said fermentation broth is adjusted to a pH of below about 2.5.

The composition may be administered at a rate of from about 1 to about 200 pounds per acre.

The invention is also directed to a method for producing a nematocidal composition comprising the steps of:

a) fermenting a bacterium or fungus to obtain a fermentation broth;

b) suspending said broth in an aqueous solution;

c) adjusting the pH of said broth in aqueous solution to a pH below about pH 2.5 with a biologically acceptable acid;

d) heating the pH-treated broth of step c) to a temperature of at least about 100° C. for at least about 15 minutes, then cooling to ambient temperature; and, e) recovering said composition;

with the proviso that said fungus is not *Myrothecium verrucaria.*

Preferably, the pH is adjusted below about 2; and most preferably, the pH is adjusted below about 1.5.

The pH of the composition formed in step d) may be adjusted to a range of about pH 4 to about pH 8. The fermentation broth of step a) may have water-soluble biomass and water-insoluble biomass; and the water-soluble biomass may be separated from said water-insoluble biomass, and the water-insoluble biomass may be suspended in aqueous solution in step b).

The invention is also directed to a method for producing a nematocidal composition comprising the steps of:

a) fermenting a bacterium or fungus to obtain a fermentation broth;

b) suspending said broth in an aqueous solution;

c) adjusting the pH of said broth in aqueous solution to a pH above about pH 8 with a biologically acceptable alkali or base;

d) heating the pH-treated broth of step c) to a temperature of at least about 100° C. for at least about 15 minutes, then cooling to ambient temperature;

e) recovering said composition.

Preferably, the pH is adjusted above about 9 and most preferably the pH is adjusted above about 10.

The pH of the composition formed in step d) may be adjusted to a range of about pH 4 to about pH 8. The fermentation broth of step a) may have water-soluble biomass and water-insoluble biomass; and the water-soluble biomass may be separated from said water-insoluble biomass, and the water-insoluble biomass may be suspended in aqueous solution in step b).

For the practice of any aspect of this invention, at least one compound such as herbicides, antimicrobials, fungicides, insecticides, plant growth regulators or nutrients may be added to the heat-treated, pH adjusted compositions.

DETAILED DESCRIPTION OF THE INVENTION

To produce a nematocidal preparation, a substantial amount of biomass is prepared by submerged fermentation of a bacterium or fungal microorganism. Preferred examples of microorganisms include *Baccillus* spp., *Myrothecium* spp., *Gibberella* spp., *Streptomyces* spp., and *Fusarium* spp. More preferred are the *Myrothecium* spp. and the *Bacillus* spp.

More specifically, the composition can be obtained from *Gibberella fujikuroi* (ATCC 12616 or 14164), *Streptomyces erythraeus* (also known as *Saccharopolyspora erythraea*, ATCC 11635 or 31772), *Bacillus sphaericus* (ATCC 4978), *Bacillus thuringiensis* such as *Bacillus thuringiensis israelensis* (ATCC 35646), *Bacillus thuringiensis kurstaki* (ATCC 33679) and *Bacillus thuringiensis* Berliner (ATCC 19268) and *Fusarium moniliforme* (ATCC 10052). The composition can be obtained from any bacterium or fungal microorganism, since the method breaks down the cell wall of the microorganism. It is believed that the cell walls of microorganisms (branched polysaccharides) are partially or completely hydrolyzed under the conditions described herein, resulting in the formation of nematocidal hydrolysis products. Therefore, the method is not microorganism-specific.

The material is suspended or dissolved in an aqueous solution, preferably water, and is hydrolyzed by acidification to a pH below about pH 2.0 by means of a biologically acceptable acid such as, for example, sulfuric, hydrochloric or phosphoric acid, or organic acids such as acetic or formic acid, and heated at a temperature of at least about 100° C. for a period of at least about fifteen minutes. The material that is treated in this manner is preferentially the water-insoluble portion of the biomass from the fermentation, and the insoluble material may be separated from the water-soluble portion of the fermentation product, but separation is not necessary. The entire fermentation broth produced in the fermentor may be treated by the process of this invention. After the mixture has been acidified and heated, it will often be appropriate to readjust the pH of the mixture to a more neutral pH to enhance safety of handling and to reduce the risk of damage to plants which would be treated with the preparation. Said pH adjustment may be carried out by addition of any biologically-acceptable alkali or base, such as sodium hydroxide, potassium hydroxide, magnesium oxide, magnesium hydroxide, calcium oxide, calcium hydroxide, or ammonia solution (ammonium hydroxide).

Alternatively, the treatment can also be achieved by raising the pH to above about pH 8 by means of alkalization with biologically-acceptable alkali or base such as, for example, sodium hydroxide, potassium hydroxide, magnesium oxide, magnesium hydroxide, calcium oxide, calcium hydroxide, or ammonia solution (ammonium hydroxide), then heating the resulting mixture as above. Again, after heating, it may be appropriate to adjust the pH of the resulting mixture to a more neutral pH by means of a biologically acceptable acid such as, for example, sulfuric, hydrochloric or phosphoric acid, or organic acids such as acetic or formic acid.

The heating step may be performed at a pressure above atmospheric pressure, if necessary. For example, elevated pressure may be achieved by heating within an autoclave.

The product thus produced is used to protect plants or control the growth of nematodes by applying it in solid form or as a suspension in aqueous solution, preferably water, directly to the surface or the root zone of the soil in which the plants are grown.

An advantage of the method which we have discovered is that the nematocidal composition is inexpensive and safe. The materials employed in the process include the fermentation broth, comprising the water-insoluble solids contained in such broth, which may be waste solids from any industrial fermentation process, such as a fermentation carried out to prepare pharmaceutical or agricultural products, or foods or beverages, and ordinary acids and bases. Previously employed industrial processes for production of nematocidal preparations are chemical syntheses which use dangerous and toxic starting materials and result in waste streams of high toxicity which must be disposed of.

The method involves a post-treatment of a fermentation material, which can be industrial fermentation waste, to produce a nematocidal composition.

As used herein the terms "nematocide" or "nematocidal", and the phrases "prevent plant damage" and "control of growth", with respect to nematodes, include not only the rapid, direct killing of nematodes, but also the concept of repelling nematodes, the prevention or effective control of their multiplication or reproduction, the prevention of nematode egg hatching, and confusing or immobilizing the nematodes so that they are prevented from finding a mate or a plant to parasitize.

The methods of using the compositions of this invention for nematode control are by application to any field, fruit, vegetable, floral or ornamental crop or nursery crop that is sensitive to attack by plant parasitic nematodes, particularly the *Meloidogyne* species. Methods of application are well-known in the art and include direct application to the soil, either as a liquid or a dried solid, controlled release of the bioactive components from solid formulations into the surrounding soil, application to the plant roots directly before planting in the soil, foliar application and the like.

The term "soil", used herein is intended to include all media capable of supporting the growth of plants and may include humus, sand, silt, loam, manure, compost and commercial potting mixtures among others.

The term "fermentor", as used herein refers to apparatus used for various types of fermentation methods including, but not limited to, shaken culture, solid-state, continuous and batch fed methods that are contemplated for production of the fermentation broths of this invention in both laboratory and large scale fermentation processes.

The term "biologically acceptable acid", as used herein refers to acids such as sulfuric acid, phosphoric acid, hydrochloric acid, acetic acid or formic acid.

The term "biologically acceptable alkali or base", as used herein refers to bases such as sodium hydroxide, potassium hydroxide, magnesium oxide, magnesium hydroxide, calcium oxide, calcium hydroxide or ammonium hydroxide.

The process of this invention may utilize various media for the initial culture growth and can consist of potato-dextrose agar, hay infusion agar, corn meal agar, leaf litter agar, PCNB agar, soil infus on (modified), or Yeast Malt Agar as are defined in the *Manual of Industrial Microbiology and Biotechnology*, Demain and Solomon, American Society of Microbiology, Washington, D.C., 1986.

According to one embodiment of this invention, fermentation is carried out in shake-flasks or in stationary-vat fermentors. In shake-flasks, aeration is provided by agitation of the flask which causes mixing of the medium with air. In the stationary fermentors, agitation is provided by impeller means such as a disc turbine, vaned disc, open turbine, or marine propeller; and aeration is accomplished by injecting air or oxygen into the fermentation mixture.

The fermentation medium consists of suitable sources of carbon, nitrogen, inorganic salts, and growth factors assimilable by the microorganism. Suitable examples of carbon sources are various sugars such as dextrose, glucose, lactose, and maltose, starch, dextrin, corn meal and glycerol.

The sources of nitrogen can be of organic, inorganic or mixed organic/inorganic origin. Examples of nitrogen sources that can be used in the culture medium are soybean meal, corn steep liquor, peanut meal, cottonseed meal, corn germ meal, fish meal, lard water, and various ammonium salts.

The inclusion of certain amounts of minerals and growth factors in the fermentation medium is also helpful. Crude medium ingredients such as distillers' solubles, corn steep liquor, fish meal, yeast products, peptonized milk and whey contain not only minerals but growth factors. However, inorganic salts such as potassium phosphate, sodium chloride, ferric sulfate, calcium carbonate, cobalt chloride, magnesium sulfate, and zinc sulfate can be added to the fermentation medium.

Solid materials, such as calcium carbonate may be added in this process, to help with pH control, which sometimes favors particular types of pellet formation for best results.

The process of producing the fermentation materials for use in this invention, while utilizing a shaken culture fermentation technique may also use such a technique for the initial stages or inoculum production as well. Production cultures are started from specially grown inocula. Growth is generally rapid at first. It then slows down and a stationary phase is usually reached. The production yield depends on the quantity of cells present, their specific activity, and the span of their product-forming capacity.

The inoculum is placed in a liquid medium which is selected empirically for its ability to allow the recovery of the majority of the cells in the population. The spores produced on an initial growth medium, such as potato-dextrose agar, are transferred into growth medium contained in a flask (termed seed flask), that would allow for the germination and initial growth of culture. The germinated spores in an active growth state are then transferred to Erlenmeyer flasks (shake-flasks) or stationary-vat fermentors containing the specific fermentation medium. A 1–2% inoculum is typically produced for the fermentation stage of development.

The inoculum medium is within the purview of those skilled in the art, and additional information may be found in the *Manual of Industrial Microbiology and Biotechnology*, pages 31–40, supra.

A wide range of shaker-culture apparatus may be used in the practice of this invention. The main types of apparatus are based on either rotary or reciprocating shaking machines. The process herein preferably uses rotary shakers in which the flasks move in orbits of about 50 mm at about 200 to about 250 rpm, (but may vary between 100 and 500 rpm). The culture moves smoothly around the inside of the flask (which is usually an Erlenmeyer flask). The scale-up of the fermentation process is well known to those skilled in the art.

The purpose of shaking in submerged culture is to supply oxygen and nutrients to the growing cells. In shaken cultures, the medium in the fermentation flasks is inoculated with cells or spores, as is the case herein. The strain used as an inoculum is held as a master culture, in the freeze-dried state or at reduced temperatures, such as $-70°$ C. The optimal spore concentration to be used for the inoculum is easily determined by those skilled in the art by routine experimentation.

The biopesticidal compositions of the present invention can be used against plant parasitic nematodes, including, for example, *Meloidogyne* spp., *Pratylenchus* spp., *Radopholus similis*, *Ditylenchus dipsaci*, *Heterodera* spp., *Xiphinema* spp., *Globodera* spp. and *Hoplolaemus* spp.

The processed fermentation materials prepared according to the process of this invention can be used to control nematodes for a variety of agricultural applications on many different plants and fruits including, but not limited to, artichokes, aubergines, banana, barley, beet roots, cacao, carrots, cassava, celery, chickpea, citrus, coconut, coffee, cole crops, corn, cotton, cowpea, eggplant, field bean, forages, ginseng, grape, guava, various lettuces, melons, millet, oat, okra, ornamentals, papaya, peanut, pepper, pigeon pea, pineapple, potatoes, rice, rye, sorghum, soybean, sugar beet, sugar cane, sweet peppers, sweet potato, tea, tobacco, tomatoes, turf, wheat and yam. Cultivated flowers can be protected according to the present invention, such as carnations, rose bushes, gerberas, chrysanthemums, pot plants, philodendrons, ferns, figs, pothos, sanseverias, and cacti; examples of nursery plants would include all the ornamental and flowering shrubs.

The bioactive materials can be incorporated into the soil of flower pots or containers, by direct application to the area to be treated at the time of planting, or up to several days earlier, or by application in a controlled release form. Application to field or orchard crops can be by granule dispersement on the surface with turnover of the soil by a claw cultivar or a light plow, generally to about 10 cm up to about 20 cm depth of soil. As the nematocide is water soluble, a drip irrigation method for application is also possible.

The compositions of the present invention can be in a suitable form for direct application or as a concentrate or primary composition which requires dilution with a suitable quantity of water or other diluent before application. The pesticidal concentration will vary depending upon the nature of the particular formation, specifically whether it is a concentrate or to be used directly.

The nematocidally effective amount of the active materials will depend upon the population of the nematode expected to be encountered, the nematode type, soil, crop, and moisture. In general, the composition may be applied at a field rate of from about 1 to about 200/lbs per acre; preferably at a rate of from about 5 to about 100/lbs per acre and most preferably at a rate of from about 10 to about 60 lbs/acre. The nematocidal compositions may be in the form of a suspension, a solution, an emulsion, a dusting powder, a dispersible granule, a wettable powder, an emulsifiable concentrate, an aerosol or impregnated granule, formulated by techniques well known to those skilled in the art.

Additives to these compositions may include surface active agents, inert carriers, preservatives, humectants, feeding stimulants, attractants, encapsulating agents, binders, emulsifiers, dyes, U.V. protectants, buffers, flow agents, or other components which facilitate product handling and application for protection against nematodes.

Examples of inert carriers include inorganic minerals such as kaolin, mica, gypsum, fertilizer, phyllosilicates, carbonates, sulfates, or phosphates; organic materials such as sugar, starches or cyclodextrins; or botanical materials such as wood products, cork, powdered corn cobs, rice hulls, peanut hulls and walnut shells.

Suitable surface active agents include anionic compounds such as carboxylates, for example an alkali metal carboxylate of a long chain fatty acid; an N-acylsarcosinate; mono- or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkyl benzene sulfonates or lower alkyl naphthalene sulfonates such as butyl naphthalene sulfonate; salts or sulfonated naphthalene-formaldehyde condensates; salts of sulfonated phenol-formaldehyde condensates or more complex sulfonates such as the amide sulfonates. Non-ionic agents include condensation products of fatty acid esters, fatty alcohols, fatty acid amides or fatty alkyl- or alkenyl-substituted phenols with ethylene oxide, fatty esters of polyhydric alcohol ethers, such as sorbitan fatty acid esters, condensation products of such esters with ethylene oxide, such as polyoxyethylene sorbitan fatty acid esters, block copolymers of ethylene oxide and propylene oxide, and acetylenic glycols. Examples of cationic surface active agents include an aliphatic mono-, di-, or polyamine as an acetate, naphthenate or oleate; an oxygen containing amine such as an amine oxide of polyoxyethylene alkylamine; an amide-linked amine prepared by the condensation of a carboxylic acid with a di- or polyamine; or a quaternary ammonium salt.

It is also contemplated that the materials of this invention may be used in combination with other essential biologicals or beneficial microorganisms or active ingredients, such as herbicides, anti-microbials, fungicides, insecticides, plant growth regulators or nutrients.

The compositions of this invention may also be formulated as active mixtures which may include finely divided dry or liquid diluents, extenders, fillers, conditioners, and excipients, including various clays, diatomaceous earth, talc and the like, or water and various organic liquids and mixtures thereof.

Of course, the present invention is not limited to the particular embodiments and modes of operation described herein and it is possible to imagine a number of variations in the details without departing from the scope of this invention.

The examples below are presented to describe preferred embodiments and utilities of the invention and are not meant to limit the invention unless otherwise stated in the claims appended hereto.

EXAMPLE 1

Water-insoluble materials were isolated from a *Myrothecium verrucaria* fermentation broth by centrifuging. These solids were washed by re-suspending in distilled water and centrifuged again. The washing process was repeated twice more, and the solids were recovered in powder form by freeze-drying. This powdered material was subsequently treated by suspending a weighed amount of it in water and heating only, or heating within several acidic environments (as detailed in Table 1 below). The materials resulting from these conditions were readjusted to pH 4, freeze dried into a powder, and tested in a contact assay with RKN. All heat treatments were carned out at 121° C. for four hours in an autoclave. Groups of approximately 50 nematodes for each replicate were incubated in 12½% aqueous suspensions of each of the reconstituted materials for a period of 24 hours, then counted to determine the percent mortality of RKN. The materials resulting from heating under acid conditions of pH 2 or lower showed significant increases in nematocidal activity.

TABLE 1

Contact Nematocidal Assay for Fermentation Samples (Insoluble Fermentation Fraction)

| Sample | Treatment | Average % Mortality of RKN[1] |
|---|---|---|
| A | Heated | 5 |
| B | pH 3 + Heated | 7 |
| C | pH 2 + Heated | 88 |
| D | pH 1.5 + Heated | 100 |
| E | pH 1.25 + Heated | 100 |
| F | Untreated | 5 |

1 = Second stage juveniles of RKN, *Meloidogyne incognita*.

EXAMPLE 2

Filter cakes (washed, damp fermentation solids) from two fungal fennentations were re-suspended in three times their weight of water, adjusted to pH 2.0 with sulfuric acid and heated in an autoclave at 121° C. for three hours. The samples were cooled, re-adjusted to pH 4.05–4.10 with sodium hydroxide solution and made up with distilled water to a final weight eight times that of the cake used (12.5% concentration). Groups of approximately 50 root-knot nematodes for each replicate were incubated for 24 hours in these suspensions as well as a distilled water control and counted to determine mortality. The heat-treated fungal fermentation solids showed strong nematocidal activity, as indicated in Table 2.

TABLE 2

| Nematodes Exposed to | Average Percent Mortality |
|---|---|
| sterile water | 0 |
| heated *Streptomyces erythraeus* solids | 97.2 |
| heated *Gibberella fujikuroi* solids | 98.5 |

EXAMPLE 3

Dry material was recovered by lyophilization from a suspension of fermentation solids from an unclassified *Streptomyces* species. The solid material (4.56 g) was re-suspended in 40 mL of water, adjusted to pH 1.9 with sulfuric acid and heated at 121–122° C. for three hours. After cooling, the pH was re-adjusted to 4.0 with sodium hydroxide solution, giving a final suspension containing 9% by weight of the fermentation solids. Groups of approximately 50 root-knot nematodes for each replicate were incubated for 24 hours with this suspension or with an antibiotic control solution (100 units of penicillin plus 0.1 mg of streptomycin per mL) and then counted to determine mortality. The heat-treated fermentation solid suspension was effective in killing the plant-parasitic nematodes, as shown in Table 3.

TABLE 3

| Nematodes Exposed to | Average Percent Mortality |
|---|---|
| Antibiotic control | 0.4 |
| Heated suspension of *Streptomyces* solids | 100 |

EXAMPLE 4

Water-insoluble materials were isolated from a *Myrothecium* fermentation broth by centrifuging as described in Example 1. This insoluble fraction was acid treated by suspending a weighed amount in water and adjusting to pH 1.72. The sample was divided and one portion was heated at 120° C. for three hours while the other portion was kept at room temperature. The materials were both readjusted to pH 4 and lyophilized into a powder. The powders were reconstituted and used in a test measuring percent mortality of root knot nematodes. Nematodes were incubated in solution for 24 hours, then counted to determine living and dead nematodes, as shown in Table 4. Reducing the pH to 1.72 and heating increased the percent mortality of root-knot nematodes.

TABLE 4

Effects of pH changes on contact nematocidal activity

| Sample | Treatment | Avg. % Mortality[2] |
|---|---|---|
| Insoluble fermentation fraction | Heated at pH 1.72 | 96.3 |
| Insoluble fermentation fraction - Control | Unheated at pH 1.72 | <1% |

[2]= Activity against second-stage juveniles of RKN, *Meloidogyne incognita*

EXAMPLE 5

Effects of Acid Digestion on Nematocidal Activity of Fermentation Broths (Greenhouse Evaluation)

Whole *myrothecium* fermentation culture broth was divided into two portions. One portion was treated by reducing the pH to 1.5 and heating at 121° C. for two hours, then readjusting the pH to 4. The other portion was an untreated control. The resulting materials were freeze-dried into a powder. The powders were reconstituted in water to equal concentrations by weight and dosed at a rate of 1.0 gram/pot onto small soil pots containing cucumber seedlings and approximately 800 root-knot nematodes per pot. The plants were maintained with light and water for one week, then removed from the soil. The galls (root swellings resulting from infection by root-knot nematode, *Meloid-* ogyne incognita) on each root were counted to determine the rate of nematode infection. Efficacy is measured by the percent gall reduction from the untreated, nematode infected control plants. As shown in Table 5, acid treated and heated fermentation broth was effective at reducing the nematode infection by about 80%, whereas fermentation broth that was not acid treated and heated controlled about 30% of the galling.

TABLE 5

| Sample | % Gall Control |
|---|---|
| Fermentation Broth (FB) | 29.46 |
| Acid Treated FB | 80.62 |

The above materials were also tested in a contact assay where root-knot nematodes were incubated for 24 hours in reconstituted solutions made from the lyophilized powders. Material that was acid treated and heated increased the percent mortality of the nematodes, whereas the untreated broth and broth that was heated without the acid treatment showed low mortality of the nematodes, as shown in Table 6.

TABLE 6

| Treatment of RKN | Average % Mortality |
|---|---|
| Fermentation Broth - unmodified | 3.5 |
| Fermentation Broth - heated | 3.4 |
| Fermentation Broth - heated under acidic conditions | 100 |

EXAMPLE 6

Nematocidal Activity of Acid-or Alkali Digested Fermentation Samples (Contact Assay)

*Myrothecium* fermentation broth was heated in acid and basic (alkaline) conditions, and the efficacy of the resulting materials was compared in a nematocidal assay (% mortality of root knot nematodes). The control broth sample was adjusted to neutral pH (pH 7), and other samples were adjusted to acidic (pH 2) and basic (pH 12) conditions. Half of each sample was heated at 121° C. for two hours. Once cooled, all the samples were readjusted to neutral pH and lyophilized (dried to a powder). The powders were reconstituted in water to equal concentrations by weight and tested in a contact assay. The contact assay consisted of RKN incubated for 24 hours in five concentrations of each material, with multiple replications. The nematodes were counted, and the number of dead nematodes determined for each concentration for every sample. Data from this test was analyzed by PROBIT analysis to determine the $LC_{50}$ (lethal concentration or dose to obtain an estimated 50% mortality of the nematodes within 95% confidence range). Fermentation broth when heated in either acid or basic conditions showed increased toxicity to nematodes, indicated by a lower $LC_{50}$ value for these materials, as shown in Table 7. Materials that were pH adjusted but not heated did not show a significant increase of toxicity to nematodes.

TABLE 7

| | $LC_{50}$ against *M. incognita* | |
|---|---|---|
| Sample | Unheated | Heated |
| Fermentation Broth (FB) pH 7 | 3.59 | 5.54 |
| FB acid condition (pH 2) | 3.58 | 1.01 |
| FB alkaline condition (pH 12) | 2.52 | 0.88 |

When plant parasitic nematodes are placed in direct contact with the compositions so produced, the nematodes are paralyzed or killed, depending on the concentration of the composition applied. When the soil in which potted plants are growing is treated with a suspension of the product produced according to the method of this invention, and then inoculated with plant parasitic nematodes, after a growing period of several days, the plants are healthier, with larger and heavier aerial parts than untreated plants similarly inoculated with nematodes. The roots of the treated plants also exhibited fewer root galls (symptoms of nematode attack and invasion) than the untreated plants. In the field, the composition produced may be applied as a suspension in water or as a dry granular material to the plants to be protected from parasitic nematodes.

EXAMPLE 7

Portions of whole fermentation beer from the submerged fermentation of *Myrothecium* sp. were adjusted to pH's of 4, 8, 9, 10 or 1 (±0.1) with sulfuric acid or sodium hydroxide and heated in an autoclave for two hours at 121° C. Control samples were pH adjusted but not heated. After heating, the samples were cooled to room temperature, and all samples were adjusted to pH 4.1 (±0.1) using sulfuric acid. Then samples were diluted to a final concentration of 2% solids. Groups of *Meloidogyne incognita* (root-know nematodes, RKN) were incubated in the suspensions as well as a dilute antibiotic control solution (1 unit/mL of penicillin and 0.1 mg/mL of streptomycin), and after 24 hours live and dead individuals were counted. Beer samples heated at elevated pH demonstrated increased nematocidal activity over non-heated samples, as shown in Table 8.

TABLE 8

| Whole-Beer Alkaline Heat Treatment | | |
|---|---|---|
| | Percent Mortality of RKN at 2% Concentration | |
| | Heated | Non-heated |
| pH 4 | 8.3 | 5.7 |
| pH 8 | 6.4 | 0.0 |
| pH 9 | 18.5 | 1.8 |
| pH 10 | 33.3 | 0.0 |
| pH 11 | 32.3 | 2.1 |
| antibiotic control | NA | 0.0 |

All References Cited are Hereby Incorporated by Reference.

The present invention is illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

Changes can be made in the composition, operation and arrangement of the method of the present invention described herein without departing from the concept and scope of the invention as defined in the following claims:

We claim:

1. A method for improving biopesticidal activity of materials produced by fermentation comprising the steps of:

fermenting a bacterium or fungus to obtain a fermentation broth;

adjusting the pH of said fermentation broth to a pH of below about 2.5 with a biologically acceptable acid, or to a pH of above about 8 with a biologically acceptable alkali or base; and heat treating said fermentation broth to a temperature of at least about 100° C. for at least about 15 minutes, then cooling to ambient temperature to obtain a pH-adjusted, heat treated composition having improved biopesticidal activity;

with the proviso that said fungus is not *Myrothecium verrucaria* when the pH of said fermentation broth is adjusted to a pH of below about 2.5.

2. The method of claim 1 wherein said fungus or bacterium is selected from the group consisting of *Gibberella fujikuroi, Streptomyces erythraeus, Bacillus sphaericus, Bacillus thuringiensis* and *Fusarium moniliforme*.

3. A method for control of nematodes on plants which comprises the step of administering to the locus, soil or seed of plants in need of such treatment, a nematocidally effective amount of a composition formed by heating a pH adjusted fermentation broth from a fungus or bacterium;

wherein said broth is adjusted to a pH of below about 2.5 with a biologically acceptable acid, or to a pH of above about 8 with a biologically acceptable alkali or base; and wherein said broth is heated to at least 100° C. for at least 15 minutes;

with the proviso that said fungus is not *Myrothecium verrucaria* when the pH of said fermentation broth is adjusted to a pH of below about 2.5.

4. The method of claim 3 wherein said composition is administered at a rate of from about 1 to about 200 pounds per acre.

5. The method of claim 3 wherein said fungus or bacterium is selected from the group consisting of *Gibberella fujikuroi, Streptomyces erythraeus, Bacillus sphaericus, Bacillus thuringiensis* and *Fusarium moniliforme*.

6. The method of claim 3 wherein said composition further comprises at least one compound selected from the group consisting of herbicides, antimicrobials, fungicides, insecticides, plant growth regulators and nutrients.

7. A method for producing a nematocidal composition comprising the steps of:

a) fermenting a bacterium or fungus to obtain a fermentation broth;

b) suspending said broth in an aqueous solution;

c) adjusting the pH of said broth in aqueous solution to a pH below about pH 2.5 with a biologically acceptable acid;

d) heating the pH-treated broth of step c) to a temperature of at least about 100° C. for at least about 15 minutes, then cooling to ambient temperature; and, e) recovering said composition;

with the proviso that said fungus is not *Myrothecium verrucaria*.

8. The method of claim 7 wherein said pH is adjusted below about 2.

9. The method of claim 7 wherein said pH is adjusted below about 1.5.

10. The method of claim 7 further comprising adjusting pH of said composition formed in step d) to a range of about pH 4 to about pH 8.

11. The method of claim 7 further comprising adding at least one compound to said composition of step e), said compound selected from the group consisting of herbicides, antimicrobials, fungicides, insecticides, plant growth regulators and nutrients.

12. The method of claim 7 wherein said fermentation broth of step a) has water-soluble biomass and water-insoluble biomass.

13. The method of claim 7 wherein said water-soluble biomass is separated from said water-insoluble biomass, and said water-insoluble biomass is suspended in aqueous solution in step b).

14. A method for producing a nematocidal composition comprising the steps of:

a) fermenting a bacterium or fungus to obtain a fermentation broth;

b) suspending said broth in an aqueous solution;

c) adjusting the pH of said broth in aqueous solution to a pH above about pH 8 with a biologically acceptable alkali or base;

d) heating the pH-treated broth of step c) to a temperature of at least about 100° C. for at least about 15 minutes, then cooling to ambient temperature;

e) recovering said composition.

15. The method of claim 14 wherein said pH is adjusted above about 9.

16. The method of claim 14 wherein said pH is adjusted above about 10.

17. The method of claim 14 further comprising adjusting pH of said composition formed in step d) to a range of about pH 4 to about pH 8.

18. The method of claim 14 further comprising adding at least one compound to said composition of step e), said compound selected from the group consisting of herbicides, antimicrobials, fungicides, insecticides, plant growth regulators and nutrients.

19. The method of claim 14 wherein said fermentation broth of step a) has water-soluble biomass and water-insoluble biomass.

20. The method of claim 19 wherein said water-soluble biomass is separated from said water-insoluble biomass, and said water-insoluble biomass is suspended in aqueous solution in step b).

* * * * *